(12) United States Patent
Zacharias et al.

(10) Patent No.: US 6,213,993 B1
(45) Date of Patent: Apr. 10, 2001

(54) SELF-ADHERING ABSORBENT ARTICLE

(75) Inventors: Duane Kenneth Zacharias, Neenah; Yung Hsiang Huang, Appleton; Frank Gerald Druecke, Oshkosh, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 826 days.

(21) Appl. No.: 08/659,858

(22) Filed: Jun. 7, 1996

Related U.S. Application Data

(63) Continuation of application No. 08/331,072, filed on Oct. 28, 1994, now abandoned.

(51) Int. Cl.$^7$ .................................................. A61F 13/15
(52) U.S. Cl. ........................ 604/386; 604/387; 604/389; 604/390
(58) Field of Search .................................. 604/386, 387, 604/389, 390

(56) References Cited

U.S. PATENT DOCUMENTS

| | | |
|---|---|---|
| 446,610 | 2/1891 | Osgood . |
| 716,265 | 12/1902 | McAllister . |
| 733,504 | 7/1903 | Nash . |
| 797,094 | 8/1905 | Benario . |
| 977,730 | 12/1910 | Guttmann . |

FOREIGN PATENT DOCUMENTS

| | | |
|---|---|---|
| 306502 | 4/1952 | (CH) . |
| 26 44 032A1 | 4/1978 | (DE) . |
| 29 30 929A1 | 2/1981 | (DE) . |
| 42 04 986A1 | 8/1993 | (DE) . |
| 0025611B1 | 11/1982 | (EP) . |
| 03 53 972 B1 | 1/1994 | (EP) . |
| 1155492 | 5/1958 | (FR) . |
| 2044433 | 2/1971 | (FR) . |
| 20808 | of 1897 | (GB) . |
| 713838 | 8/1954 | (GB) . |
| 781975 | 8/1957 | (GB) . |
| 2041757 | 9/1980 | (GB) . |
| 2048684 | 12/1980 | (GB) . |
| 2115431 | 9/1983 | (GB) . |
| 63-260554 | 10/1988 | (JP) . |
| 5-7222 | 2/1993 | (JP) . |
| 6-9622 | 2/1994 | (JP) . |
| 89/00106 | 1/1989 | (WO) . |
| 89/06950 | 8/1989 | (WO) . |
| 91/15250 | 10/1991 | (WO) . |
| 93/00118 | 1/1993 | (WO) . |
| 95/16424 | 6/1995 | (WO) . |
| 832380 | of 1983 | (ZA) . |

OTHER PUBLICATIONS

Viscoelastic Properties of Polymers, John D. Ferry, John Wiley & Sons, third edition, pp. 264–280 (1980).

Studies of Triblock Copolymer–Tackifying Resin Interactions by Viscoelasticity and Adhesive Performance, Mon Fu Tse, Journal of Adhesion Science Technology, vol. 3, No. 7, pp. 551–570 (1989).

Test Procedure ASTM–D 4440–84. pp. 482–484 (1985).

Standard Trauma (Tape Stripping) in Human Vulvar and Forearm Skin, Acta Derm Venereol (Stockh) (1991) 71: 123–126.

Medical–Grade Acrylic Adhesives for Skin Contact, Kenny et al. Journal of Applied Polymer Science, vol. 45, 355–361 (1992).

*Primary Examiner*—John G. Weiss
*Assistant Examiner*—Paul Shanoski
(74) *Attorney, Agent, or Firm*—Thomas J. Connelly; Thomas M. Parker; Douglas G. Glantz

(57) ABSTRACT

An absorbent article is provided having an adhesive on the bodyfacing surface for securement of the article to the wearer. The adhesive has a rheological property tan δ at 20° C. ranging from about 0.01 to about 0.6 at a frequency of about 0.1 radian per second and a tan δ ranging from about 0.1 to about 1.7 at a frequency of about 1000 radians per second. Preferably the adhesive is a hot melt adhesive.

9 Claims, 9 Drawing Sheets

U.S. PATENT DOCUMENTS

| | | | |
|---|---|---|---|
| 1,441,656 | 1/1923 | Bosse . | |
| 1,861,530 | 6/1932 | Hayden et al. . | |
| 2,068,703 | 1/1937 | Powdermaker . | |
| 2,310,082 | 2/1943 | Holbrooke | 128/156 |
| 2,349,709 | 5/1944 | Evans | 117/44 |
| 2,399,545 | 4/1946 | Davis | 128/156 |
| 2,512,713 | 6/1950 | Cahill | 128/290 |
| 2,592,801 | 4/1952 | Hanington | 128/156 |
| 2,740,403 | 4/1956 | Schueler | 128/156 |
| 2,742,903 | 4/1956 | Lightner | 128/290 |
| 2,861,006 | 11/1958 | Salditt | 117/7 |
| 2,940,868 | 6/1960 | Patchell | 117/38 |
| 3,039,893 | 6/1962 | Banigan, Jr. et al. | 117/122 |
| 3,315,677 | 4/1967 | Tyrrell, Jr. | 128/288 |
| 3,342,183 | 9/1967 | Edenbaum | 128/268 |
| 3,438,371 * | 4/1969 | Fischer et al. | 604/387 |
| 3,457,919 | 7/1969 | Harbard | 128/156 |
| 3,512,530 | 5/1970 | Jones, Sr. | 128/290 |
| 3,672,371 | 6/1972 | Roeder | 128/290 |
| 3,756,232 | 9/1973 | Noguchi et al. | 128/290 R |
| 3,783,072 | 1/1974 | Korpman | 156/244 |
| 3,805,790 | 4/1974 | Kaczmarzyk et al. | 128/290 R |
| 3,811,438 | 5/1974 | Economou | 128/156 |
| 3,885,559 | 5/1975 | Economou | 128/156 |
| 3,897,783 | 8/1975 | Ginocchio | 128/290 R |
| 3,897,784 | 8/1975 | Fitzgerald | 128/290 R |
| 3,906,952 | 9/1975 | Zamist | 128/290 R |
| 3,908,658 | 9/1975 | Marsan | 128/283 |
| 3,972,328 | 8/1976 | Chen | 128/156 |
| 4,024,312 | 5/1977 | Korpman | 428/343 |
| 4,072,151 | 2/1978 | Levine | 128/290 R |
| 4,079,739 | 3/1978 | Whitehead | 128/290 R |
| 4,080,348 | 3/1978 | Korpman | 260/27 BB |
| 4,123,409 | 10/1978 | Kaelble | 260/29.1 |
| 4,192,785 | 3/1980 | Chen et al. | 260/17.4 |
| 4,233,978 | 11/1980 | Hickey | 128/295 |
| 4,321,924 | 3/1982 | Ahr | 128/287 |
| 4,333,466 | 6/1982 | Matthews | 128/290 R |
| 4,337,772 | 7/1982 | Roeder | 128/290 R |
| 4,367,732 | 1/1983 | Poulsen et al. | 128/156 |
| 4,389,211 | 6/1983 | Lenaghan | 604/383 |
| 4,393,080 | 7/1983 | Pawelchak et al. | 428/355 |
| 4,418,123 | 11/1983 | Bunnelle et al. | 428/517 |
| 4,421,737 | 12/1983 | Ito et al. | 424/28 |
| 4,455,146 | 6/1984 | Noda et al. | 604/897 |
| 4,460,364 | 7/1984 | Chen et al | 604/387 |
| 4,485,087 | 11/1984 | Otsuka et al. | 424/28 |
| 4,538,603 | 9/1985 | Pawelchak et al. | 128/156 |
| 4,551,490 | 11/1985 | Doyle et al. | 524/22 |
| 4,552,802 | 11/1985 | Mechin | 428/255 |
| 4,593,053 | 6/1986 | Jevne et al. | 523/111 |
| 4,655,768 | 4/1987 | Marecki et al. | 604/897 |
| 4,693,776 | 9/1987 | Krampe et al. | 156/327 |
| 4,699,134 | 10/1987 | Samuelsen | 128/156 |
| 4,699,146 | 10/1987 | Sieverding | 128/640 |
| 4,699,792 | 10/1987 | Nick et al. | 424/446 |
| 4,701,177 | 10/1987 | Ellis et al. | 604/385 |
| 4,701,509 | 10/1987 | Sun et al. | 526/264 |
| 4,711,781 | 12/1987 | Nick et al. | 424/446 |
| 4,732,808 | 3/1988 | Krampe et al. | 428/355 |
| 4,733,659 | 3/1988 | Edenbaum et al. | 128/156 |
| 4,738,676 | 4/1988 | Osborn, III | 604/385 R |
| 4,743,249 | 5/1988 | Loveland | 424/447 |
| 4,753,648 | 6/1988 | Jackson | 604/389 |
| 4,762,888 | 8/1988 | Sun et al. | 525/125 |
| 4,773,408 | 9/1988 | Cilento et al. | 128/156 |
| 4,775,374 | 10/1988 | Cilento et al. | 604/344 |
| 4,781,713 | 11/1988 | Welch et al. | 604/385.1 |
| 4,784,653 | 11/1988 | Bolton et al. | 604/307 |
| 4,793,337 | 12/1988 | Freeman et al. | 128/156 |
| 4,804,380 | 2/1989 | Lessen et al. | 604/385.1 |
| 4,833,193 | 5/1989 | Sieverding | 524/486 |
| 4,855,335 | 8/1989 | Neperud | 523/111 |
| 4,879,118 | 11/1989 | Senuma et al. | 424/448 |
| 4,911,948 | 3/1990 | McIntyre | 427/45.1 |
| 4,949,668 | 8/1990 | Heindel et al. | 118/314 |
| 4,950,264 | 8/1990 | Osborn, III | 604/385.1 |
| 4,951,658 | 8/1990 | Morgan et al. | 128/163 |
| 4,963,361 | 10/1990 | Kawazi | 424/443 |
| 4,983,109 | 1/1991 | Miller et al. | 425/7 |
| 4,995,333 | 2/1991 | Keller et al. | 118/300 |
| 4,995,382 | 2/1991 | Lang et al. | 128/156 |
| 5,009,653 | 4/1991 | Osborn, III | 604/385.1 |
| 5,030,303 | 7/1991 | Cucuzza | 156/164 |
| 5,032,403 | 7/1991 | Sinnerich | 424/448 |
| 5,051,259 | 9/1991 | Olsen et al. | 424/443 |
| 5,059,189 | 10/1991 | Cilento et al. | 604/307 |
| 5,068,103 | 11/1991 | Kawazi et al. | 424/81 |
| 5,089,267 | 2/1992 | Hille et al. | 424/449 |
| 5,098,500 | 3/1992 | Reed et al. | 156/253 |
| 5,112,889 | 5/1992 | Miller et al. | 524/77 |
| 5,114,419 | 5/1992 | Daniel et al. | 604/385.1 |
| 5,123,900 | 6/1992 | Wick | 602/41 |
| 5,126,144 | 6/1992 | Jaeger et al. | 424/448 |
| 5,147,698 | 9/1992 | Cole | 428/40 |
| 5,152,282 | 10/1992 | Elphick et al. | 604/180 |
| 5,176,916 | 1/1993 | Yamanaka et al. | 424/448 |
| 5,219,341 | 6/1993 | Serbiak et al. | 604/361 |
| 5,244,457 | 9/1993 | Karami et al. | 602/55 |
| 5,254,348 | 10/1993 | Hoffman et al. | 424/449 |
| 5,270,358 | 12/1993 | Asmus | 524/55 |
| 5,273,757 | 12/1993 | Jaeger et al. | 424/448 |
| 5,445,627 * | 8/1995 | Mizutani et al. | 604/387 |

* cited by examiner

SELF-ADHERING ABSORBENT ARTICLE

This application is a continuation of application Ser. No. 08/331,072 entitled "SELF-ADHERING ABSORBENT ARTICLE" and filed in the U.S. Patent and Trademark Office on Oct. 28, 1994, now abandoned. The entirety of this application is hereby incorporated by reference.

FIELD OF THE INVENTION

The present invention relates to a disposable absorbent article having an adhesive disposed adjacent to a wearer's skin. More particularly, the invention relates to a catamenial device having a supportive adhesive residing on the bodyside surface of the device.

BACKGROUND OF THE INVENTION

All manner and variety of externally positioned disposable absorbent articles configured for the absorption of body fluids such as menses, urine, feces and the like are well known. For simplicity of describing the invention, such articles will be collectively referred to herein as a sanitary napkin. Those skilled in the art understand the differences in these structures and will readily appreciate the adaptability of this invention to these other structures.

Securement of the sanitary napkin during use is often accomplished by attaching the sanitary napkin to the wearer's undergarment by a pressure sensitive adhesive. Securing a sanitary napkin to an undergarment can exhibit a number of drawbacks. One drawback is that the adhesive can stick too aggressively to the inside surface of the undergarment leaving residue. Another disadvantage is the napkin will tend to move with the undergarment rather than associating with the bodily movements of the wearer. This can result in a less secure fit and increase the incidence of fluid leakage, irritation, chafing and discomfort.

In the past, attempts have been made to adhere a sanitary napkin to the wearer. However, the sanitary napkins have been large enough so as to avoid the adhesive being placed in contact with the wearer's pubic hair and sensitive genitalia. This is because in securing the sanitary napkin to the wearer, the prior art teaches using adhesives of the type used in various surgical applications. Removal of these adhesives typically causes sudden pain and discomfort to the wearer. Thus, avoiding such sensitive areas has been desirable.

It would therefore be desirable to have a sanitary napkin that can be secured to the wearer's body that would be comfortable to wear, would be discrete, give the wearer a feeling of security during use and would not cause discomfort upon removal.

SUMMARY OF THE INVENTION

Briefly, this invention relates to an absorbent article having an absorbent core with at least one surface designed to be positioned adjacent to a wearer's body, i.e., having a bodyfacing surface, and a pressure sensitive adhesive secured to the bodyfacing surface. Preferably the adhesive is a hot melt adhesive. Adhesives in accordance with the present invention have a rheological property, tan delta ($\delta$) referenced to 20° C., ranging from about 0.01 to about 0.6 and preferably from about 0.06 to about 0.48 at a frequency of 0.1 radians per second and a tan $\delta$ ranging from about 0.10 to about 1.7 and preferably from about 0.20 to about 1.5 at a frequency of 1000 radians per second. In a preferred embodiment of the invention the absorbent article includes a cover wherein the adhesive is secured to the bodyfacing surface of the cover.

The general object of this invention is to provide an absorbent article that is adhesively attached to the wearer's body. A more specific object of this invention is to provide a sanitary napkin that uses one or more adhesives having specific rheological properties to secure the sanitary napkin to the wearer.

Another object of the invention is to provide a sanitary napkin that is comfortable to wear and can be readily removed with little or no pain or discomfort to the wearer.

Other objects and advantages of the present invention will become more apparent to those skilled in the art in view of the following description and the accompanying drawings.

DETAILED DESCRIPTION OF THE PREFERRED EMBODIMENT

The present invention relates generally to disposable absorbent articles that are secured to the body of a wearer by a pressure sensitive adhesive and preferably a hot melt, pressure sensitive adhesive. For convenience of description only, the invention will be described as applied to a catamenial device, i.e. a sanitary napkin, but the invention is not limited thereto. As used herein, the term "sanitary napkin" refers to an article which is worn by females adjacent to the pudendal region and which is intended to absorb and contain various exudates which are discharged from the body, such as, blood, menses and urine. The sanitary napkin is intended to be discarded after a single use. Interlabial devices which reside partially within and partially external of the female wearer's vestibule are also within the scope of this invention. It is to be understood that the invention may be adapted for use in other absorbent articles such as diapers, incontinent devices and the like.

Figure 1:
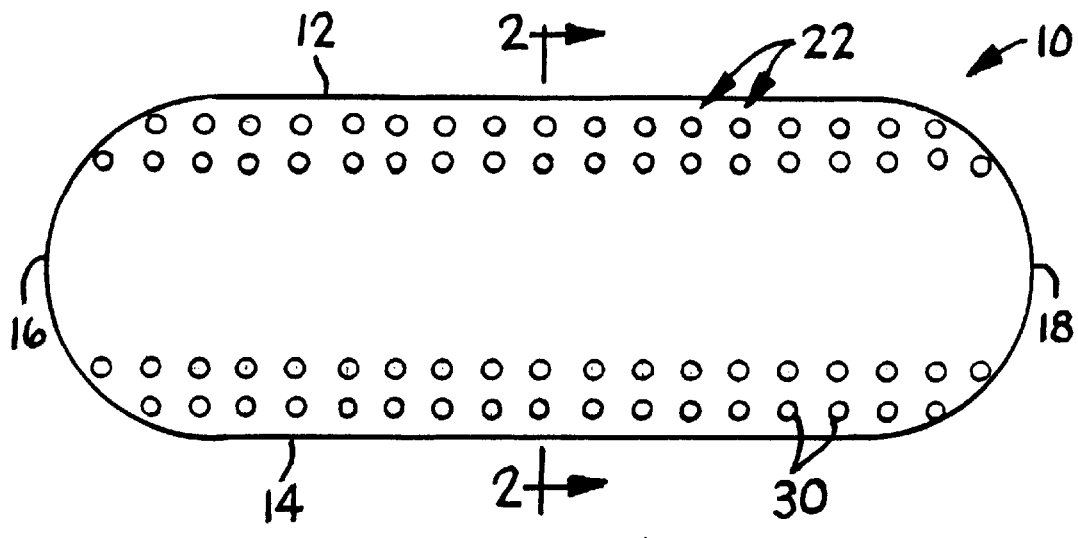
FIG. 1 is a top plan view of an absorbent article showing one embodiment of the invention.
Figure 2:
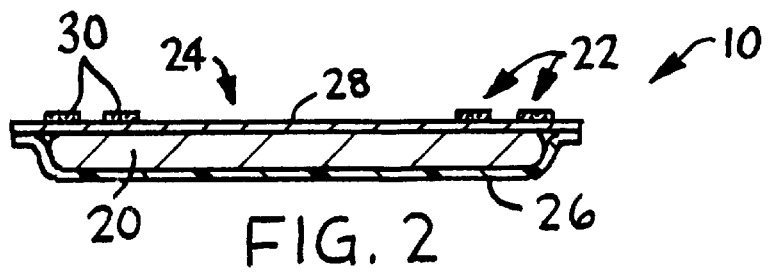
FIG. 2 is a cross-sectional view of FIG. 1 taken along line 2—2.

For ease of understanding when referring to the figures, similar numerals designate like parts in the different views and embodiments. Referring to FIGS. 1 and 2, an embodiment of a sanitary napkin 10 is shown. Although depicted as having generally race track shape, the sanitary napkin 10 can have any variety of shapes well known to those skilled in the art. For example, hourglass, oval etc. In the most basic embodiment, the sanitary napkin 10 has a pair of longitudinal sides 12 and 14, transverse ends 16 and 18, an absorbent core 20 and a bodyside adhesive 22. The sanitary napkin 10 has at least one major surface 24 adapted to be positioned adjacent to a wearer's body. That is, the surface 24 is soft and liquid-permeable. Positioned distally from the bodyfacing surface 24 is a fluid-impermeable baffle 26.

The absorbent core 20 may be any material which is generally compressible, comfortable, non-irritating to the wearer's skin and capable of absorbing and containing body exudates such as urine, menses, blood and the like. Desirably, the absorbent core 20 maintains its integrity when wetted during use. The absorbent core 20 can be manufactured into different shapes and from a variety of liquid-absorbent materials commonly known in the disposable absorbent article art. For example, absorbent materials such as cellulose fibers, wood pulp, regenerated cellulose or cotton fibers can be used. Such fibers may be chemically or physically modified. The absorbent core 20 may include any of the above fibers in combination with other materials, both natural and synthetic, such as hydrophilic foams, hydrophilic polymers or the like. Wood pulp is frequently the material of choice primarily because it is inexpensive and readily available. The absorbent core 20 may also include a thin absorbent layer of material such as tissue, fabric or the like made of cellulosic fibers. The absorbent core 20 can also include one or more superabsorbent materials known in the art. By "superabsorbent" we mean a hydrocolloid material that is capable of absorbing an amount of water which is at least ten times the weight of the hydrocolloid particles in the dry form and preferably from about 15 to 70 times the dry weight. Such materials are further described in U.S. Pat. No. 5,247,072 issued on Sep. 21, 1993 to Ning et al. the disclosure of which is incorporated herein and made a part hereof.

The baffle 26 which is typically liquid-impermeable, can be designed to permit the passage of air and moisture vapor to the outer surface while blocking the passage of liquids. The baffle 26 may be made from one or more polymeric films such as polyethylene, polypropylene, cellophane, or a film/nonwoven laminate and the like. The baffle 26 can also be constructed from a liquid-permeable material that has been treated or coated to become liquid impervious.

Referring to FIG. 2, the sanitary napkin 10 includes a liquid-permeable cover 28 having a bodyfacing surface 24. The cover 28 is positioned adjacent to the absorbent core 20. The cover 28, which is designed to contact the wearer's body, can be made from various polymeric films that are apertured for fluid migration into the absorbent core, or from woven or nonwoven fibers or strands produced from natural or synthetic materials which are easily penetrated by body fluids. Thermoplastic polymer films made from polyethylene or polypropylene are preferred. Other acceptable covers might be produced by laminating film and fiber substrates. It can also be beneficial to aperture or emboss (not shown) the cover 28 to increase the rate at which the body fluids can penetrate down and into the absorbent core 20.

The bodyside adhesive 22 is positioned adjacent to the cover 28 in an open, substantially rectangular pattern of small discrete dots or adhesive members 30 so as to leave numerous areas free from adhesive. The adhesive members 30 can have a surface area of about 0.03 square centimeters ($cm^2$) to about 20 $cm^2$ and preferably about 0.15 $cm^2$ to about 15 $cm^2$. As measured from the bodyfacing surface 24 of the cover 28, the adhesive members 30 can have a thickness of about 0.01 millimeters to about 2 millimeters. The dot pattern of FIG. 1 contains approximately the least amount of bodyside adhesive 22 required to obtain sufficient adherence to achieve the desired result and provide a satisfactory removal comfort. Generally, the adhesive 22 is secured to less than about 90 percent of the area of the bodyfacing surface 24, preferably less than about 70 percent of the area and most preferably less than about 20 percent of the area.

It is to be understood that any suitable adhesive pattern may be selected for applying the adhesive 22 to the bodyfacing surface 24 of the sanitary napkin 10, provided it is consistent with the concentration of adhesive 22 desired on the bodyfacing surface 24 yet allowing the sanitary napkin 10 to retain the requisite amount of absorbency. For example, adhesive patterns can be oval, swirls, various linear or non-linear arrays of adhesive longitudinally and/or transversely oriented and reticulated webs having unobstructed interstices between the adhesive fibers or combinations thereof. The adhesive patterns may be open or closed. By "open" it is meant that the adhesive can have an intermittent or continuous pattern that does not substantially cover one or more of the transverse ends 16 and/or 18 of the sanitary napkin 10. While "closed" means the adhesive would encircle the absorbent core 20. Preferably, the pattern of the adhesive 22 substantially corresponds to the configuration of the absorbent core 20. Desirably, the adhesive 22 is applied in a pattern that is symmetrical about an axis which bisects the sanitary napkin 10 and divides the sanitary napkin 10 into substantially equal portions. This gives the wearer a balanced feel when wearing the sanitary napkin 10. It also reduces the perception of any associated discomfort when the sanitary napkin 10 is removed from the body.

The adhesive 22 can be applied to the bodyfacing surface 24 by techniques known in the art. For example, screen printing or extruding the adhesive 22 from one or more nozzles onto the bodyfacing surface 24 as described in the commonly assigned U.S. Pat. No. 4,995,333 issued to Keller et al. on Feb. 26, 1991, the entire disclosure of which is incorporated herein and made a part hereof.

The adhesive deposited in accordance with the present invention may be any pressure sensitive adhesive, and preferably a hot melt adhesive, that is characterized as having specific Theological properties described below. Suitable adhesives include A-B-A block copolymers, A-B-B-A block copolymers, wherein A is a block polymer of monovinyl substituted aromatic hydrocarbon and B is an elastomeric block polymer of a conjugated diene. The rheological analysis of an adhesive is a method of determining the viscoelastic property of polymers. Further explanations of polymer rheology and their measurement are discussed in: *Viscoelastic Properties of Polymers*, John D. Ferry, John Wiley & Sons, third edition, pages 264–280 (1980); "Studies of Triblock Copolymer-Tackifying Resin Interactions by Viscoelasticity and Adhesive Performance", Mun Fu Tse, Journal of Adhesion Science Technology, Vol 3. No. 7, pages 551–570 (1989); and test procedure ASTM-D 4440-84 the disclosures of which are incorporated herein by reference and made a part hereof. It is critical to the present invention that the adhesive have a rheology property, tan δ (referenced to 20° Centigrade), ranging from about 0.01 to about 0.6 and preferably from about 0.06 to about 0.48 and most preferably from about 0.06 to about 0.40 at a frequency of about 0.1 radians per second and a tan δ ranging from about 0.1 to about 1.7, preferably from about 0.20 to about 1.5 and most preferably from about 0.6 to about 1.5 at a frequency of about 1000 radians per second.

Figure 10:
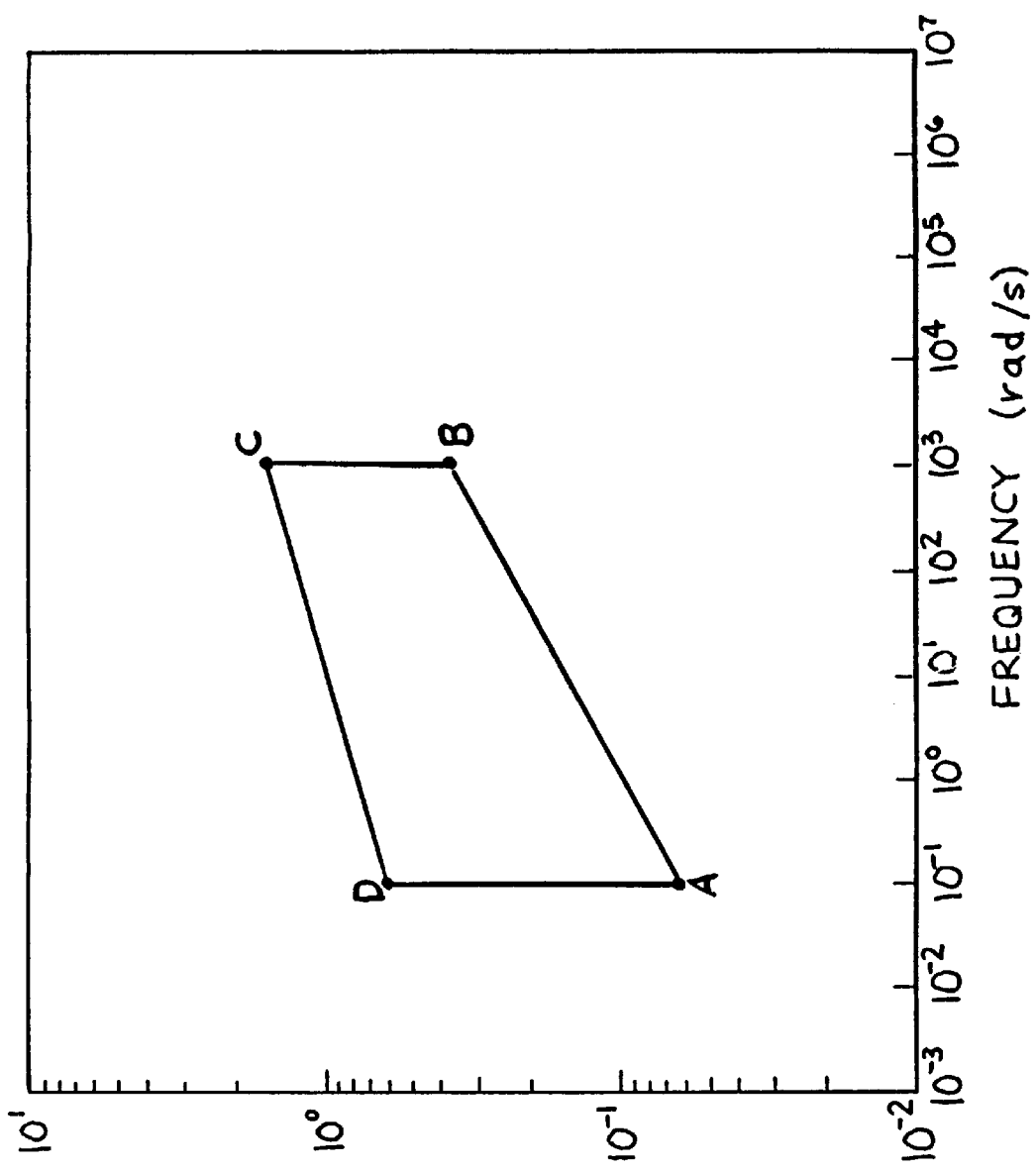
FIG. 10 is a graphical plot of frequency (in radians per second) verse the rheological property tan $\delta$ illustrating the quadrangle ABCD.

Preferred adhesives have a tan δ, (referenced to 20° Centigrade), inside the Quadrangle ABCD between the frequency range of about 0.1 radians per second to about 1000 radians per second, as seen in FIG. 10. The sides defining the Quadrangle ABCD are determined by plotting as points A, D, B and C the crucial range of tan δ described above at the lower and upper frequencies, i.e. 0.1 radians/second and 1000 radians/second, respectively. Generally, adhesives having a tan δ outside of the Quadrangle ABCD provide insufficient adhesion to support the sanitary napkin 10 to the wearer or not allowing the sanitary napkin 10 to be comfortably removed. For example, referring to FIG. 10, adhesives having tan δ values below line AB at frequencies of about 0.1 to about 100 radians per second lack sufficient flow and wet-out characteristics to provide initial adhesion or quick-stick of the sanitary napkin 10 to the body. Adhesives having a tan δ below line AB at frequencies of about 150 to about 1000 radians per second lack sufficient adhesion to keep the sanitary napkin 10 securely and comfortably attached to the body of the wearer during use.

Moreover, adhesives having tan δ values greater than line CD, at frequencies of about 0.1 radians per second to about 100 radians per second lack sufficient cohesive strength to remain in place on the sanitary napkin 10 during storage, use and removal. While adhesives having a tan δ greater than line CD at frequencies of about 150 to about 1000 radians per second cause discomfort during removal of the soiled sanitary napkin 10.

Especially preferred adhesives have a Secondary Transition Frequency peak within the Quadrangle ABCD and a Primary Transition Frequency peak at a frequency greater than about 1000 radians per second, as seen in FIGS. 6–9. The "Primary Transition Frequency" and "Secondary Transition Frequency" peaks are determined by amplitude. The peak having the greater amplitude is the primary peak regardless of its occurrence in the frequency sweep. The peaks are determined by graphically plotting, on a log/log scale, the frequency (in radians per second) verse tan δ (referenced to 20° C.) of the adhesive 22 using a time-temperature superposition master curve between the frequencies of about 0.001 and $10^7$ radians per second. These curves are determined using a Rheometrics Dynamic Spectrometer (RDS II E), which can be obtained from Rheometrics, Inc. located at 1 PossumTown Road, Piscataway, N.J. 08854. The rheological quantities for tan δ are measured on bulk adhesive samples not suspended on any substrate and having a thickness of approximately 2 to 3 millimeters. The adhesive was cut into a 25 millimeter diameter circle and placed between two 25 millimeter parallel plate fixtures of the Rheometrics Dynamic Spectrometer. The upper platen was lowered onto the sample until the normal force meter indicates a slight deflection. The samples are allowed to equilibrate at a selected test temperature before analyzing. A minicomputer governs the application of a 1% peak-to-peak shear strain to the sample. The frequency of the application can be controlled to a fraction of a radian/sec. The values of the loss tangent (tan δ) are calculated from geometry factors, peak-to-peak amplitude of the torque signal, and phase lag of the torque output wave. Typically, a computer using RHIO's software available from Rheometrics, Inc. is used to control the operation of the apparatus and to calculate values for time-temperature superposition using known techniques.

Frequency sweeps from 0.1 rad/s to 100 rad/s are run at 10° increments from −60° C. to 120° C. The Rhios software shifts the curves relative to a reference temperature of 20° C. From these shifted curves, a "master" curve can be generated.

The adhesive can be a rubber-based adhesive such as styrenebutadiene, polyisobutylene, polybutadiene and polyisoprene; a water soluble adhesive such as polyvinyl alcohol, polyvinyl acetate, and methyl cellulose; and preferably, a hot melt adhesive such as block copolymers of styrene-butadiene-styrene, styrene-isoprene-styrene, styrene-ethylenepropylene-styrene, styrene-ethylenebutylene-styrene and tetrablock copolymers such as styrene-ethylenepropylene-styrene-ethylenepropylene. Incorporated with the adhesives can be suitable tackifying resins and, if appropriate, oils. Such adhesives are available commercially from Findley Adhesives located at Watertown Plank Road, Wauwatosa Wis., 53226 and National Starch and Chemical Company, 10 Finderne Avenue, P O Box 6500, Bridgewater, N.J. 08807-3300.

Polyacrylate copolymers such as vinyl acetate-2-ethyl hexyl-acrylate combined with tackifiers, such as, for example, ethylene amine can be used but these adhesives are not preferred since they are extremely aggressive and generally cause a high level of discomfort upon removal of the sanitary napkin 10. Moreover, the acrylate adhesives can leave adhesive residue on the wearer when the sanitary napkin 10 is removed.

The present invention will be more clearly understood from the following examples, which are an exemplary nature only and are not intended to limit the scope of the invention.

COMPARATIVE EXAMPLES A–C

Three adhesives, National Starch 34-5516, National Starch 70-9908 and Findley H2292H were analyzed for their viscoelastic property, tan δ, peel strength and comfort.

Figure 3:
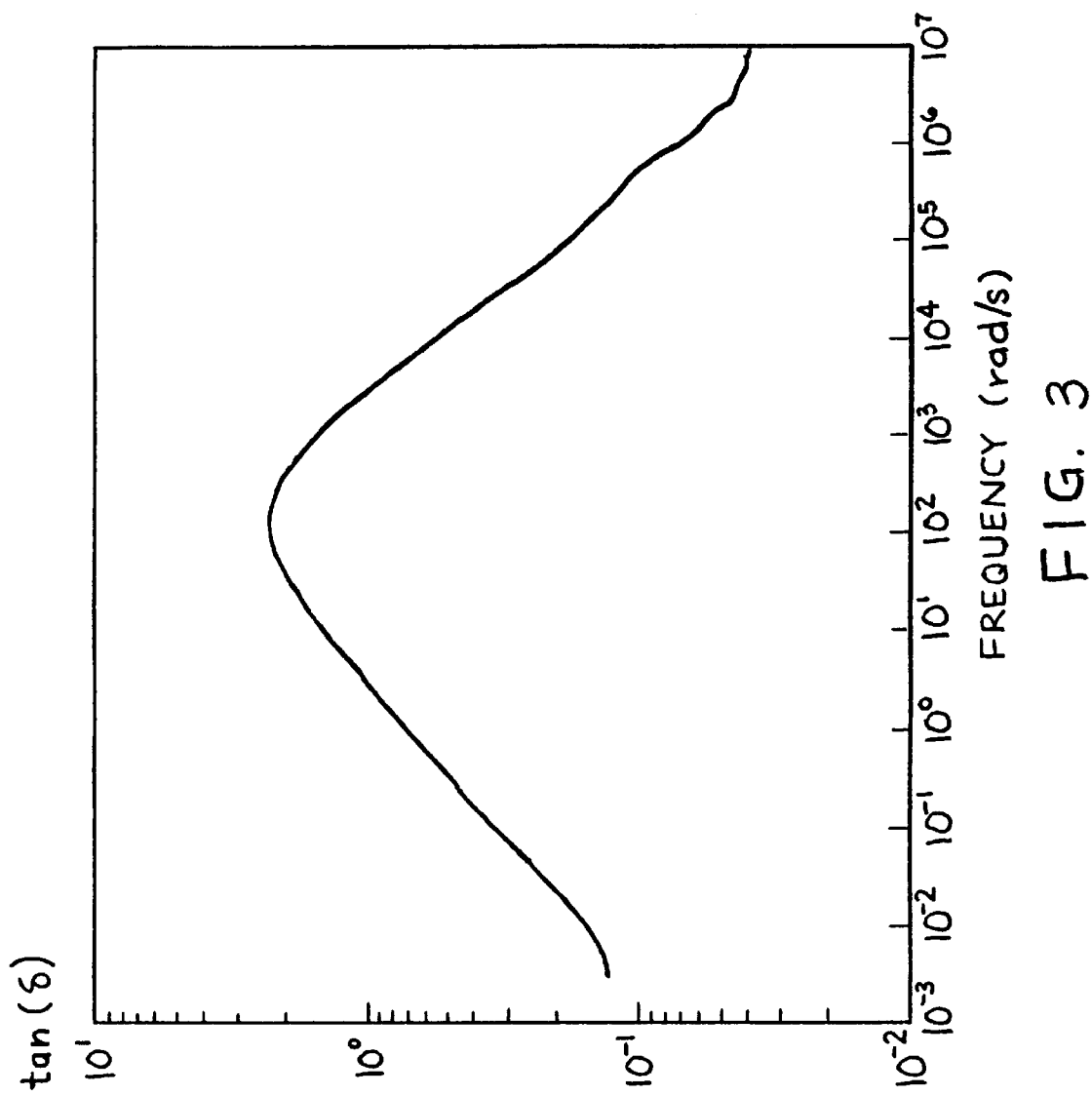
FIG. 3 is a time-temperature superposition graphical plot of the frequency (in radians per second) verse the rheological property tan $\delta$ referenced to 20° C. for National Starch adhesive 34-5516.
Figure 4:
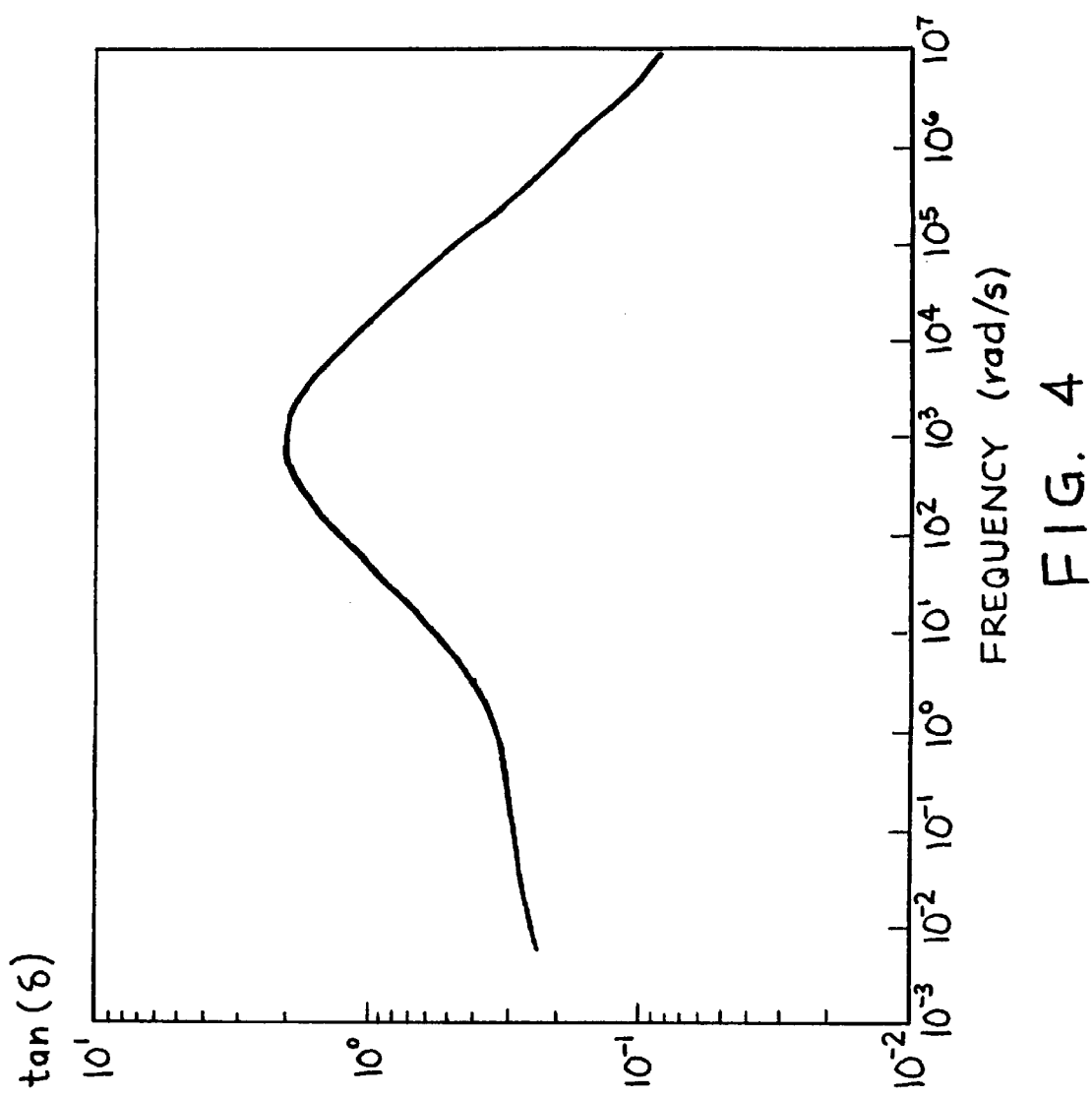
FIG. 4 is a time-temperature superposition graphical plot of the frequency (in radians per second) verse the rheological property tan $\delta$ referenced to 20° C. for National Starch adhesive 70-9908.
Figure 5:
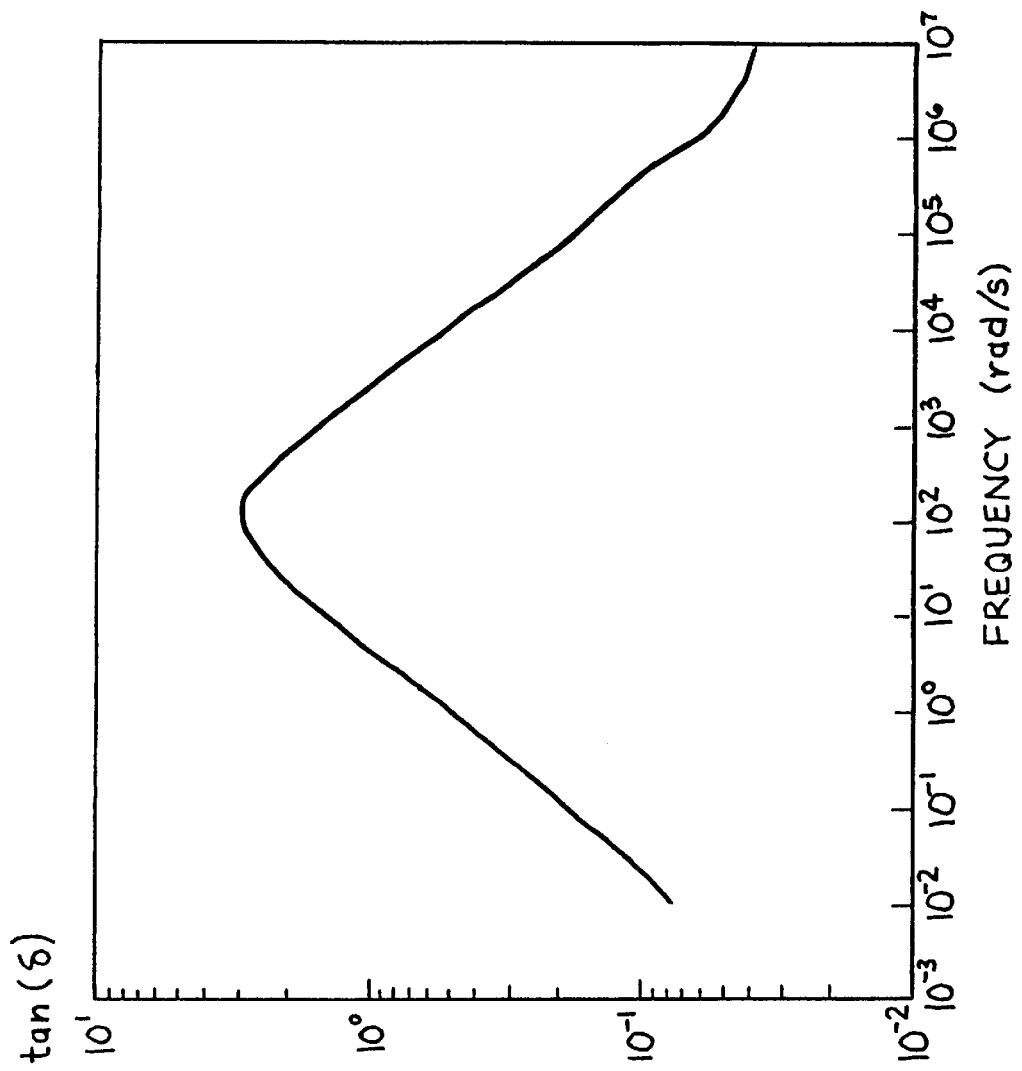
FIG. 5 is a time-temperature superposition graphical plot of the frequency (in radians per second) verse the rheological property tan $\delta$ reference to 20° C. for Findley adhesive H2292H.
Figure 6:
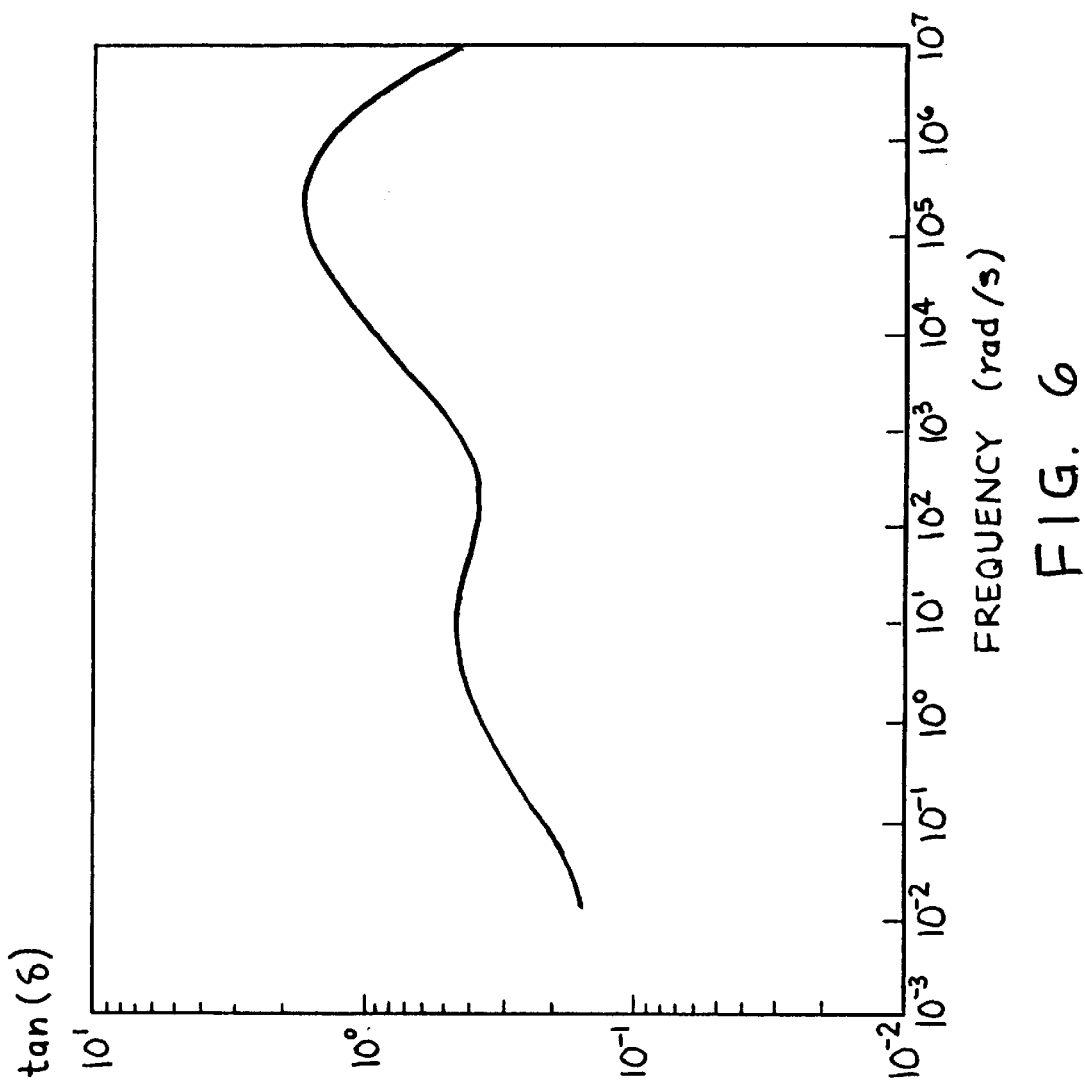
FIG. 6 is a time-temperature superposition graphical plot of the frequency (in radians per second) verse the rheological property tan $\delta$ referenced to 20° C. for National Starch adhesive 7659-42-3 in accordance with the present invention.
Figure 7:
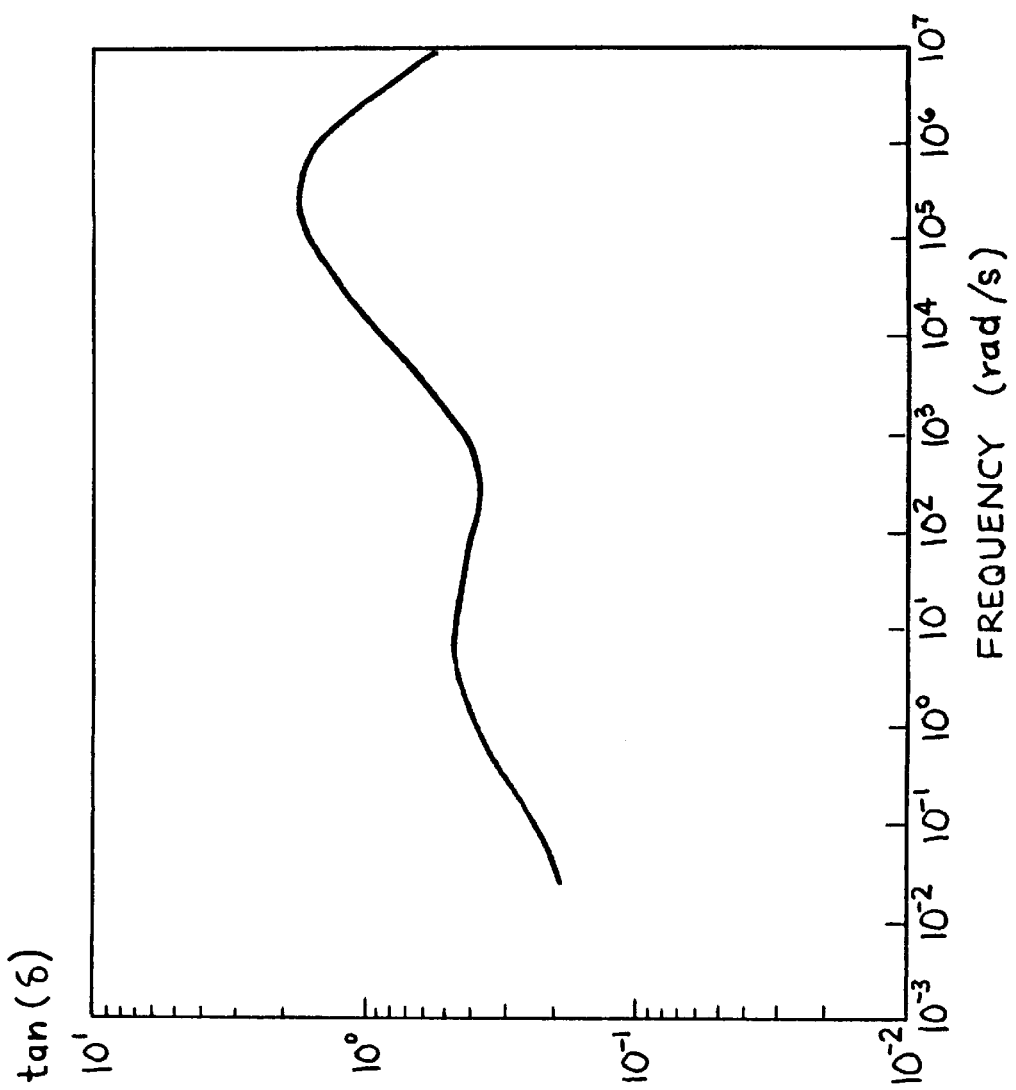
FIG. 7 is a time-temperature superposition graphical plot of the frequency (in radians per second) verse the rheological property tan $\delta$ referenced to 20° C. for National Starch adhesive 8111-60-4 in accordance with the present invention.
Figure 8:
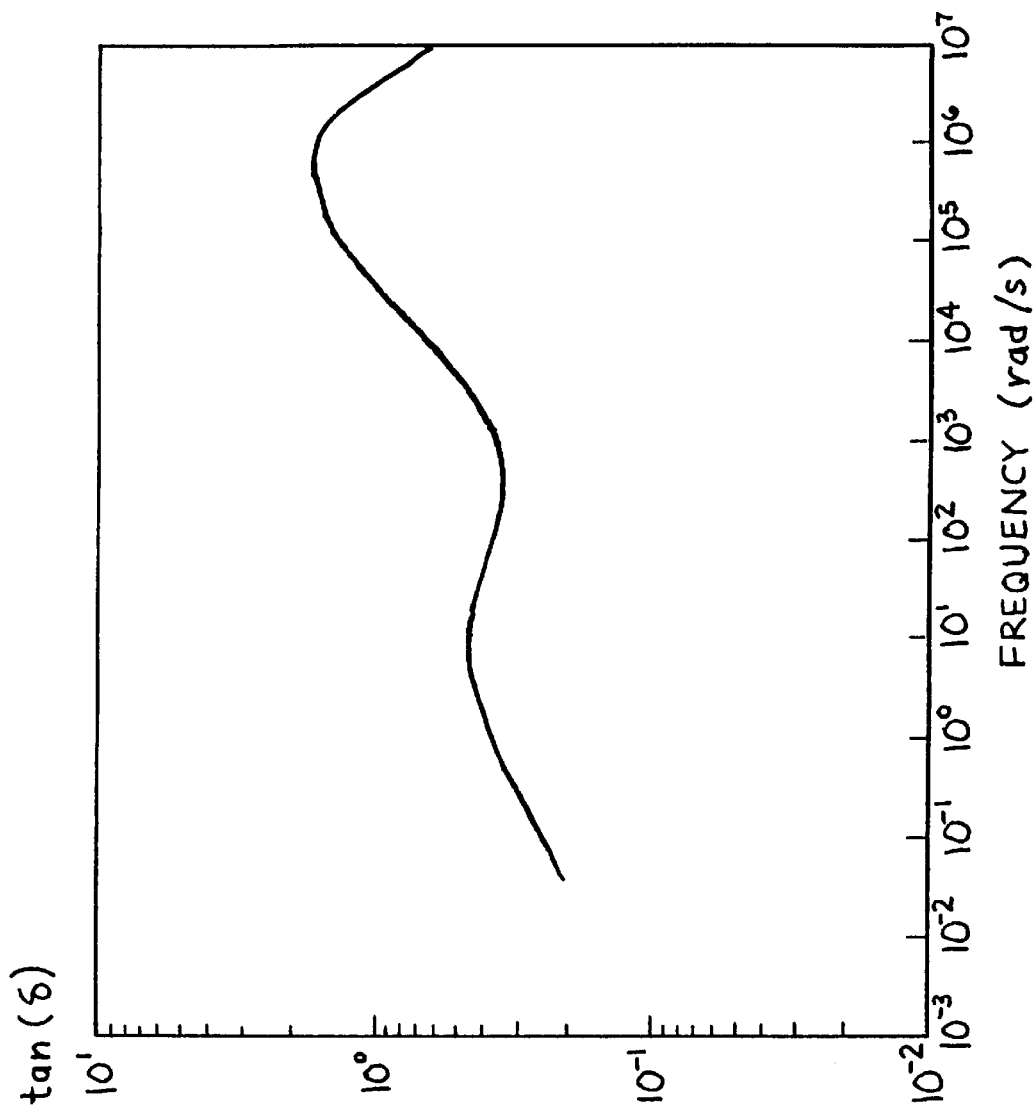
FIG. 8 is a time-temperature superposition graphical plot of the frequency (in radians per second) verse the rheological property tan $\delta$ referenced to 20° C. for National Starch adhesive 8111-69-2 in accordance with the present invention.
Figure 9:
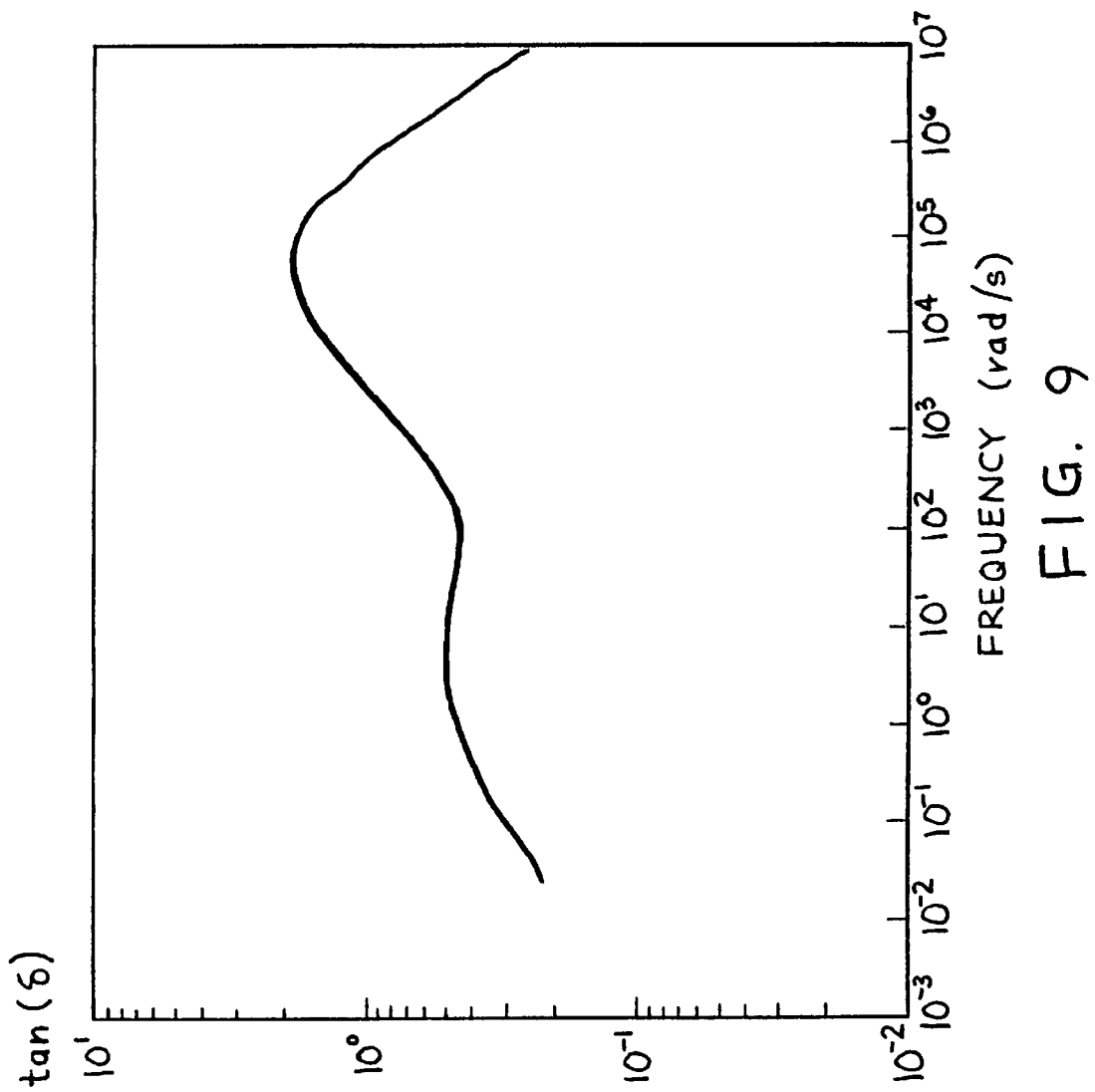
FIG. 9 is a time-temperature superposition graphical plot of the frequency (in radians per second) verse the rheological property tan $\delta$ referenced to 20° C. for National Starch adhesive 7659-41-3 in accordance with the present invention.

FIGS. 3–5 are the graphical plots of Frequency (rad/sec) vs. the viscoelastic property tan δ referenced to 20° C. for these respective adhesives. As can be seen from each graphical plot, these adhesives would not be acceptable for contacting the sensitive vulvar region.

Peel strength data was obtained by preparing adhesive test laminates as follows.

The adhesive was coated onto a substrate such as a silicone coated release paper. The adhesive pattern used for conducting the tests was two (2) lines of adhesive each approximately 6 mm wide running parallel to the longitudinal axis of the substrate. The adhesive lines were spaced about 38 millimeters apart and equidistant from the center of the laminate. The adhesive was slot coated onto a substrate using techniques known in the art. The adhesive/substrate was then contacted with a nonwoven material, spunbond polypropylene. The spunbond had a basis weight of 0.6 ounces per square yard. The substrate/spunbond laminate was subjected to a pressure ranging from about 35 pounds per square inch gauge (psig) to about 80 psig from a heated nip roller to ensure adequate transfer of the adhesive onto the spunbond material. The nip temperature ranged from about 25° Centigrade to about 150° Centigrade. Total adhesive add on to the spunbond was approximately 263 grams per square meter. Surface area covered by the adhesive was approximately 16–25 percent. The substrate was then removed and the adhesive laminates were then tested for peel strength.

The peel strength of the adhesive was determined using a modified Pressure Sensitive Tape Council 180° peel resistance test (PSTC-1) described below. PSTC-1 is a standardized test procedure that is described in greater detail on page 23 of the tenth edition of *Test Methods* copyright 1992, available from Pressure Sensitive Tape Council 401 North Michigan Ave., Chicago, Ill. 60611-4267 the disclosure of which is incorporated herein and made a part hereof. The peel adhesion values were determined according to the following procedure.

A double sided adhesive tape of approximately 13 millimeters wide was secured to the top and bottom edges of a stainless steel test plate having dimensions of about 100 millimeters wide and 152 millimeters long. The adhesive tape was 3M #665 available from the 3M Corporation located in St. Paul, Minn. A polyethylene film 0.05 millimeters thick, male embossed, was secured to the double sided tape with male embossed side as the test surface. The polyethylene film is available from Edison Plastic, located in Washington, Ga. One end of the spunbond, i.e. the end that will be the leading end, was rigidly secured to a leading strip of non-stretchable material. The leading strip should be stronger than the peel strength of the adhesive. The test sample was pressed down on the polyethylene film with a 2043 gram mechanical roller, (available from Chemsultant International, Mentor, Ohio). The 180° peel was then immediately conducted on a Materials Test System model 810 available from MTS Corp., Minneapolis, Minn. 55424. When placing the test specimen in the tester, the jaws of the tester were initially set 17.78 cm apart. The steel test panel was secured in the stationary jaw (1.27 cm) with the unsecured leading strip extending past the position of the stationary jaw. The leading strip was then doubled back and clamped in a centered arrangement within the moving jaw of the tester. The tester was activated to conduct the 180° peel test. The moving jaw travelled a total distance of 20.32 cm, with the adhesive tested in the middle 10.16 cm. The MTS can be programed to control the peel rate using a microprofiler model 458.91.

The peel strength of the three adhesives were tested in accordance with the procedure described above. The results are set forth in TABLE A below.

TABLE A

| Example | Adhesive | Peel Adhesion 100 mm/min | (grams force) 1200 mm/min | at a rate of 3500 mm/min |
|---------|----------|--------------------------|---------------------------|--------------------------|
| A | 34-5516 | 390 | >1200 | >1200 |
| B | 70-9908 | 580 | >1200 | >1200 |
| C | H2292H | 450 | >1200 | >1200 |

Comfort data were obtained by testing the adhesives on five subjects. Each subject had an average hair density of about 6 to about 20 hairs per square centimeter ($cm^2$) on the forearms. Each subject placed two (2) adhesive test members on each forearm.

Each adhesive member was composed of a substrate slot coated with the test adhesive. The substrate was composed of a nonwoven material such as spunbond polypropylene 63.5 millimeters (2.5 inches) wide. The test adhesive was slot coated onto the substrate in 2-six (6) millimeter (¼ inch) wide strips using techniques known in the art. Each adhesive strip was spaced apart by a distance of 38.1 millimeters (1.5 inches). The adhesive strips extended the length of the substrate. The first adhesive member had a length of 127 millimeters (5 inches) and the second adhesive member had a length of about 51 millimeters (2 inches).

The first adhesive member was placed on the upper portion of the subject's forearm, as viewed with the palm of the hand resting downward, with the longitudinal centerline of the adhesive member parallel to the longitudinal axis of the forearm. The second adhesive member was placed on the lower portion of the subject's forearm in a like manner. Each adhesive members was pressed down onto the subject's forearm with a force of less than about 8 pounds.

The adhesive was tested for initial tack and comfort and again after two (2) hours by removing the adhesive member from the forearm.

The test subjects evaluating the comfort of the adhesive in accordance with the procedure described above determined these three adhesives to have excessive discomfort upon removal.

EXAMPLES 1–4

Other adhesives, National Starch 7659-42-3, National Starch 811-60-4, National Starch 8111-69-2 and National Starch 7659-41-3 were analyzed as described above for Examples A–C for the viscoelastic property tan δ, peel strength and comfort. FIGS. 6–9 are graphical plots of Frequency vs. tan δ referenced to 20° C. for these respective adhesives. As can be seen from each graphical plot, these adhesives would be acceptable for contacting the sensitive vulvar region.

Peel strength of these adhesives were tested in accordance with the procedure described above for Examples A–C. The results are set forth in TABLE 1 below.

TABLE 1

| Example | Adhesive | Peel Adhesion 100 mm/min | (grams force) 1200 mm/min | at a rate of 3500 mm/min |
|---------|----------|--------------------------|---------------------------|--------------------------|
| 1 | 7659-42-3 | 90 | 430 | 700 |
| 2 | 8111-60-4 | 80 | 400 | 580 |
| 3 | 8111-69-2 | 60 | 350 | 580 |
| 4 | 7659-41-3 | 180 | 680 | 1050 |

The test subjects evaluating the comfort of these adhesives in accordance with the procedure described above determined these adhesives to not have excessive discomfort upon removal.

From the above tests, one can see the importance of having a low tan δ in the frequency region that would correspond to a removal rate for the absorbent article. While the invention has been described in conjunction with a specific embodiment, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

We claim:

1. An absorbent article comprising:
   a) a cover having a bodyfacing surface with a predetermined area and a garmentfacing surface;
   b) an absorbent core adjacent to said garmentfacing surface of said cover; and c) a hot melt, pressure sensitive adhesive secured to less than about 90 percent of said bodyfacing area, said adhesive selected from the group consisting A-B-A block copolymers and A B-B-A block copolymors, wherein A is a block polymer of mono-vinyl substituted aromatic hydrocarbon and B is an elastomeric block polymer of a conjugated diene and having a Lan $\delta$ at a frequency of about 0.1 radians per second to about 1000 radians per second residing inside a quadrangle ABCD wherein said quadrangle ABCD is defined by graphically plotting frequency in radians per second verse tan $\delta$ referenced to about 20° Centigrade of said adhesive, said quadrangle ABCD having as points A and D a tan $\delta$ of about 0.06 and 0.4 respectively at a frequency of about 0.1 radians pet second and points B and C at a tan $\delta$ of about 0.1 and about 1.7 respectively at a frequency of about 1000 radians per second.

2. The absorbent article of claim 1 wherein said adhesive is secured to less than about 70 percent of said area.

3. The absorbent article of claim 1 wherein said adhesive is secured to less than about 20 percent of said area.

4. The absorbent article of claim 1 wherein said adhesive is symmetrical about an axis wherein said axis bisects said absorbent article into substantially equal portions.

5. The absorbent article of claim 4 wherein said adhesive has a peel force ranging from about 50 grams to about 750 grams at a peel rate of about 50 millimeters per minute to about 3500 millimeters per minute.

6. The absorbent article of claim 1 wherein said adhesive includes an array of independent adhesive members, said members each having a surface area between about 0.03 cm$^2$ to about 20 cm$^2$ and a thickness of about 0.01 millimeters to about 2 millimeters.

7. An absorbent article comprising:
a) a cover having a bodyfacing surface with a predetermined area and a garmentfacing surface;
b) an absorbent core adjacent to said garmentfacing surface of said cover; and
c) a hot melt, pressure sensitive adhesive secured to less than about 90 percent of said bodyfacing area, said adhesive having a tan $\delta$ at a frequency of about 0.1 radians per second to about 1000 radians per second residing inside a quadrangle ABCD wherein said quadrangle ABCD is defined by graphically plotting frequency in radians per second verse Lan $\delta$ referenced to about 20° Centigrade of said adhesive, said quadrangle ABCD having as points A and D a tan $\delta$ of about 0.06 and 0.4 respectively at a frequency of about 0.1 radians pet second and points B and C at a tan $\delta$ of about 0.1 and about 1.7 respectively at a frequency of about 1000 radians per second, and said adhesive having a primary transition frequency peak greater than about 1000 radians per second.

8. An absorbent article comprising:
a) a cover having a bodyfacing surface with a predetermined area and a garmentfacing surface;
b) an absorbent core adjacent to said garmentfacing surface of said cover; and
c) a hot melt, pressure sensitive adhesive secured to less than about 90 percent of said bodyfacing area, said adhesive having a tan $\delta$ at a frequency of about 0.1 radians per second to about 1000 radians per second residing inside a quadrangle ABCD wherein said quadrangle ABCD is defined by graphically plotting frequency in radians per second verse tan $\delta$ referenced to about 20° Centigrade of said adhesive, said quadrangle ABCD having as points A and D a tan $\delta$ of about 0.06 and 0.4 respectively at a frequency of about 0.1 radians pet second and points B and C at a tan $\delta$ of about 0.1 and about 1.7 respectively at a frequency of about 1000 radians per second, and said adhesive having a secondary peak between a frequency range of about 0.1 and about 1000 radians per second.

9. An absorbent article comprising:
a) a cover having a bodyfacing surface with a predetermined area and a garmentfacing surface;
b) an absorbent core adjacent to said garmentfacing surface of said cover; and
c) a hot melt, pressure sensitive adhesive secured to less than about 90 percent of said bodyfacing area, said adhesive selected from the group consisting of block copolymers of styrene-butadiene-styrene, styrene-isoprene-styrene, styrene-ethylenepropylene-styrene, styrene-ethylenebutylene-styrene, and styrene-ethylenepropylene-styrene-ethylenepropylene and having a tan $\delta$ at a frequency of about 0.1 radians per second to about 1000 radians per second residing inside a quadrangle ABCD wherein said quadrangle ABCD is defined by graphically plotting frequency in radians per second verse tan $\delta$ referenced to about 20° Centigrade of said adhesive, said quadrangle ABCD having as points A and D a tan $\delta$ of about 0.06 and 0.4 respectively at a frequency of about 0.1 radians pet second and points B and C at a tan $\delta$ of about 0.1 and about 1.7 respectively at a frequency of about 1000 radians per second.

* * * * *